(12) United States Patent
Munro (10) Patent No.: US 10,087,196 B2
(45) Date of Patent: Oct. 2, 2018

(54) POLYMORPHS

(71) Applicant: VECTURA LIMITED, Chippenham Wiltshire (GB)

(72) Inventor: Alexander Munro, Chippenham (GB)

(73) Assignee: VECTURA LIMITED, Chippenham Wiltshire (GB)

( * ) Notice: Subject to any disclaimer, the term of this patent is extended or adjusted under 35 U.S.C. 154(b) by 0 days.

(21) Appl. No.: 15/547,657

(22) PCT Filed: Jan. 27, 2016

(86) PCT No.: PCT/EP2016/051691
§ 371 (c)(1),
(2) Date: Jul. 31, 2017

(87) PCT Pub. No.: WO2016/124464
PCT Pub. Date: Aug. 11, 2016

(65) Prior Publication Data
US 2018/0016284 A1 Jan. 18, 2018

(30) Foreign Application Priority Data
Feb. 5, 2015 (EP) ..................................... 15153961

(51) Int. Cl.
*C07D 519/00* (2006.01)
*A61K 47/26* (2006.01)

(52) U.S. Cl.
CPC ............ *C07D 519/00* (2013.01); *A61K 47/26* (2013.01); *C07B 2200/13* (2013.01)

(58) Field of Classification Search
CPC .................................................... C07D 519/00
See application file for complete search history.

(56) References Cited

FOREIGN PATENT DOCUMENTS

WO WO 2011/051452 A1 5/2011

OTHER PUBLICATIONS

Bernstein, "Conventions for naming polymorphs," Polymorphism Crystallography, vol. 14, p. 8 (2002).
Byrn et al., "Solid-State Chemistry of Drugs," pp. 82-85 (1999).
Caira, "Crystalline Polymorphism of Organic Compounds," Topics in Current Chemistry, vol. 198, pp. 163-208 (1998).
International Search Report for International Application No. PCT/EP2016/051691, dated Jun. 1, 2016.
Written Opinion of the International Search Authority for International Application No. PCT/EP2016/051691, dated 2016.

*Primary Examiner* — David K O'Dell
(74) *Attorney, Agent, or Firm* — Finnegan, Henderson, Farabow, Garrett & Dunner, L.L.P.

(57) ABSTRACT

The invention relates to a polymorphic forms of (S)-3-(3-(1-methyl-2-oxo-5-(pyrazolo[1,5-a]pyridine-3-yl)-1H-imidazo[4,5-b]pyridine-3(2H)-yl)piperidin-1-yl)-3-oxopropanenitrile and their use as a therapeutic agent for the treatment of respiratory diseases.

7 Claims, 5 Drawing Sheets

Figure 1

XRPD diffractogram of Compound (I) Form I

Figure 2

XRPD diffractogram of Compound (I) Form II

Figure 3

XRPD diffractogram of Compound (I) Form III

Figure 4

1H NMR spectrum of Compound (I) Form 1 and Form II

Figure 5

1H NMR spectrum of Compound (I) Form 1 and Form III

POLYMORPHS

This application is a national stage filing under 35 U.S.C. § 371 of International Application No. PCT/EP2016/051691, filed on Jan. 27, 2016, which claims priority of European Patent Application No. 15153961.6, filed Feb. 5, 2015. The contents of these applications are each incorporated herein by reference.

The present invention relates to new polymorphic forms of pharmaceutical compounds, pharmaceutical compositions containing them and their use as therapeutic agents.

WO2011/051452 discloses compounds which are useful as Janus kinase inhibitors, in particular JAK3 inhibitors. The compounds disclosed therein have utility in the treatment of various diseases, including respiratory indications such as asthma and COPD.

Drugs for the treatment of respiratory diseases are frequently administered via dry powder inhalation devices. Formulating respiratory drugs as dry powders with inhalation excipients such as lactose is complicated and unpredictable. There is a continuing need for stable dry powder formulations which exhibit desirable bioavailability and physical properties. Bioavailability and physical characteristics are important for efficient handling and processing of the drug substance, to ensure that an effective dose is delivered to the correct part of the lung, and that the drug is effective in treating respiratory diseases. Factors such as crystallinity, stability, density, flow characteristics and electrostatic charge all have a complicated influence on the handling and delivery of the drug substance.

Different formulation techniques are known in the art and can be applied to drug compounds in an attempt to produce inhalation powders having the desired physiochemical properties.

It has now been found that a drug substance disclosed in WO2011/051452, namely the compound (S)-3-(3-(1-methyl-2-oxo-5-(pyrazolo[1,5-a]pyridine-3-yl)-1H-imidazo[4,5-b]pyridine-3(2H)-yl)piperidin-1-yl)-3-oxopropanenitrile having the structure shown below and known herein as compound (I) can be prepared in different polymorphic forms. Surprisingly one form exists as a polymorph with particularly advantageous stability properties. Compound (I) as prepared following the process in WO2011/051452 is known as Form I herein.

Compound (I)

Therefore, in one embodiment the invention comprises a novel polymorphic form of (S)-3-(3-(1-methyl-2-oxo-5-(pyrazolo[1,5-a]pyridine-3-yl)-1H-imidazo[4,5-b]pyridine-3(2H)-yl)piperidin-1-yl)-3-oxopropanenitrile (Compound (I)).

In one embodiment the invention provides a polymorph of the Compound (I) selected from the polymorphs described below as Form II or Form III.

In one embodiment the invention comprises a polymorph of Compound (I) characterised in that it provides an X-ray powder diffraction pattern which shows the following diffraction angles (2Theta) using copper Kα radiation:
  at approximately 14.04°
  at approximately 16.89°
  at approximately 17.64°
  at approximately 22.14°
  at approximately 24.39°
  at approximately 24.93°
  at approximately 26.23°

The invention further comprises a polymorph of Compound (I) characterised in that it provides an X-ray powder diffraction pattern which shows the following diffraction angles (2Theta) using copper Kα radiation:
  at 14.04°, at 16.89°, at 17.64°, at 22.14°, at 24.39°, at 24.93° and at 26.23°

This polymorph is known as Form I herein.

Figure 1:
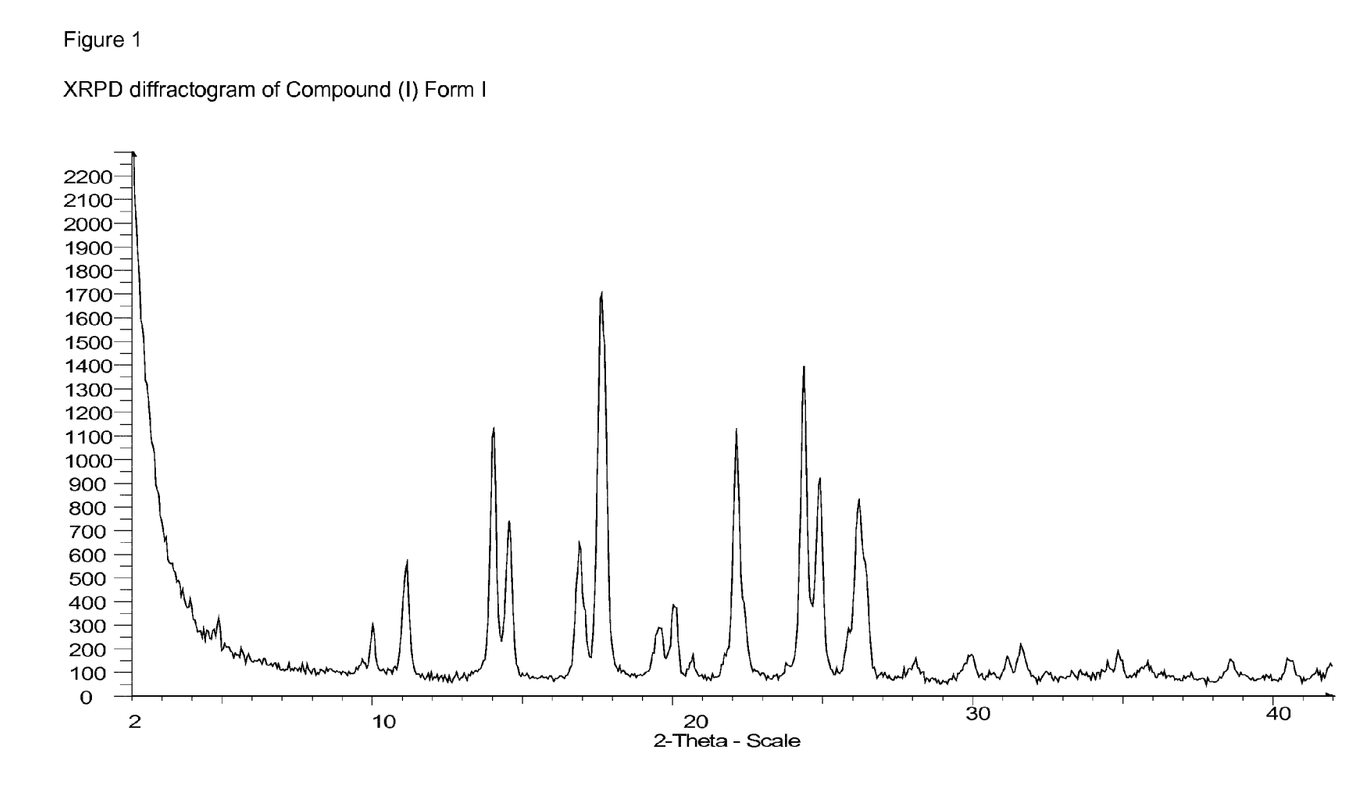
FIG. 1 shows the XPRD diffractogram of Compound (I) Form I.

The Form I polymorph is further characterised as having a XPRD diffractogram substantially as shown in FIG. 1. In one embodiment the Form I polymorph is characterised as having a XPRD diffractogram as shown in FIG. 1. The Form I polymorph is further characterised as having a DSC endotherm onset of 142° C., an exotherm onset of 155° C. and an endotherm onset of 235° C.

In one embodiment the invention comprises a polymorph of Compound (I) characterised in that it provides an X-ray powder diffraction pattern which shows the following diffraction angles (2Theta) using copper Kα radiation:
  at approximately 8.25°
  at approximately 13.25°
  at approximately 15.40°
  at approximately 17.65°
  at approximately 25.39°

The invention further comprises a polymorph of Compound (I) characterised in that it provides an X-ray powder diffraction pattern which shows the following diffraction angles (2Theta) using copper Kα radiation:
  at 8.25°, at 13.25°, at 15.40°, at 17.65° and at 25.39°

This polymorphic form is known as Form II herein.

Figure 2:
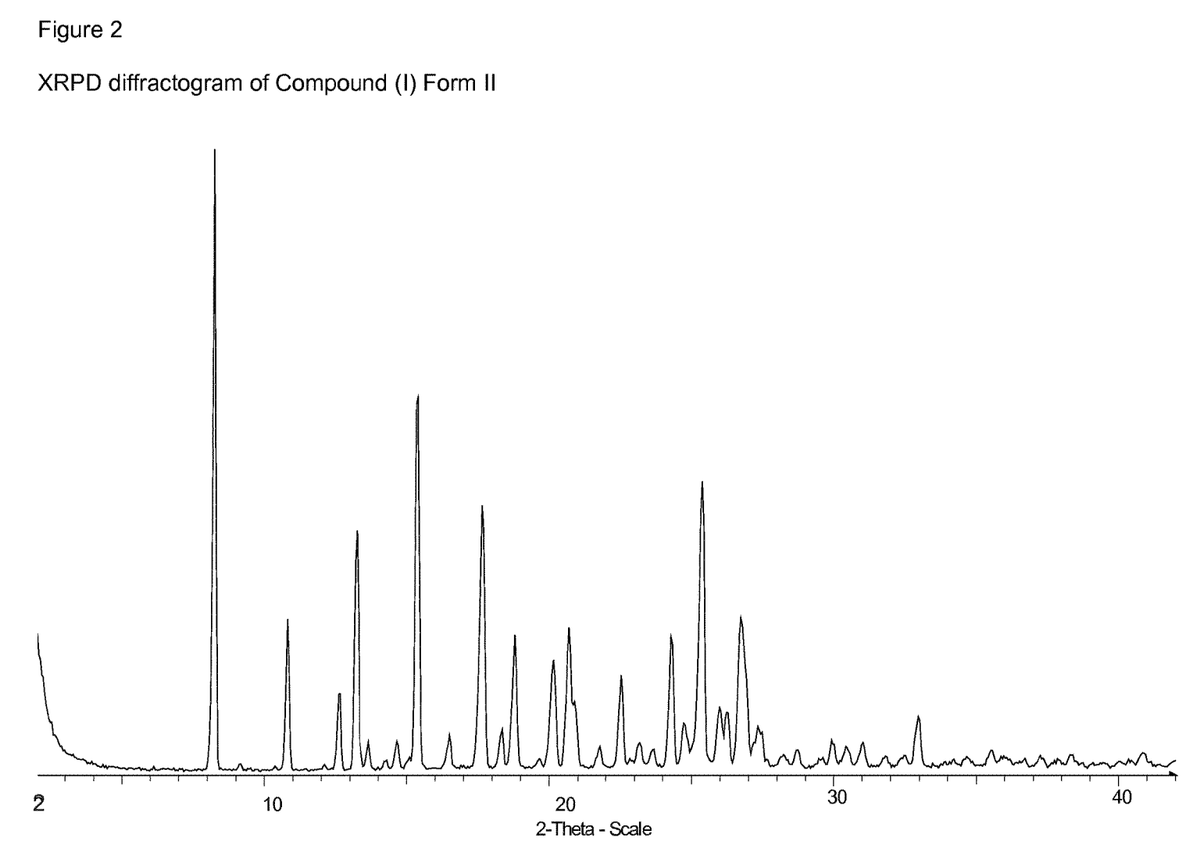
FIG. 2 shows the XPRD diffractogram of Compound (I) Form II.

The Form II polymorph is further characterised as having a XPRD diffractogram substantially as shown in FIG. 2. In one embodiment the Form II polymorph is characterised as having a XPRD diffractogram as shown in FIG. 2. The Form II polymorph is further characterised as having a DSC endotherm onset of 239° C.

The Form II polymorph exhibits greater thermodynamic stability when compared to the other polymorphic forms or the solvates and hydrates disclosed herein at temperatures up to 50° C. It is therefore more suitable as a pharmaceutical product than the other forms or the solvates and hydrates disclosed herein.

In a further embodiment the invention provides a Form III polymorph of compound (I) having the following diffraction angles (2Theta) using copper Kα radiation:
  at approximately 11.40°
  at approximately 13.60°
  at approximately 15.60°
  at approximately 22.80°
  at approximately 26.69°

The invention further comprises a Form III polymorph of compound (I) having the following diffraction angles (2Theta) using copper Kα radiation:
  at 11.40°, at 13.60°, at 15.60°, at 22.80° and at 26.69°

This polymorph is known as Form III herein.

Figure 3:
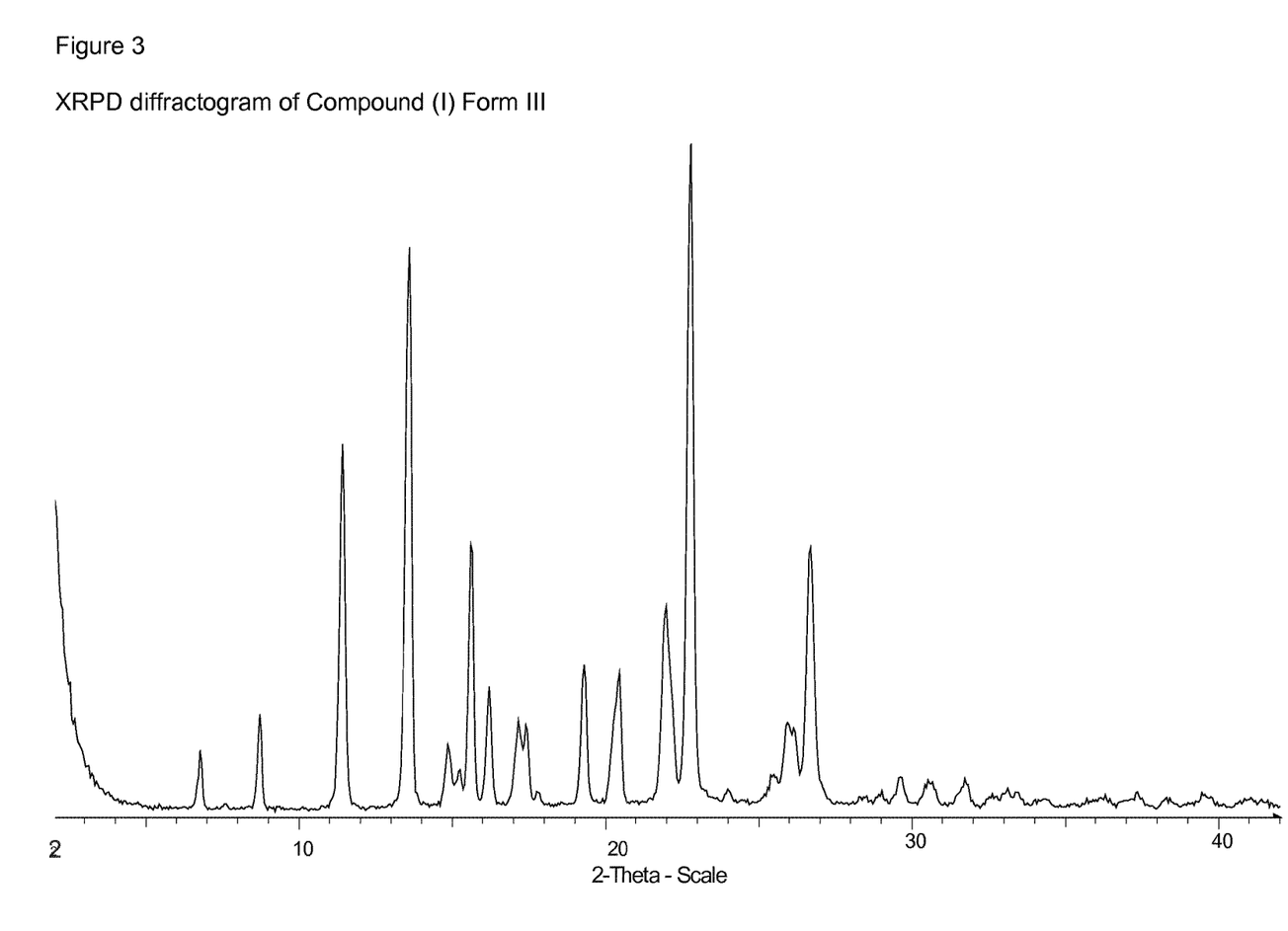
FIG. 3 shows the XPRD diffractogram of Compound (I) Form III.

The Form III polymorph is further characterised as having a XPRD diffractogram substantially as shown in FIG. 3. In one embodiment the Form III polymorph is further characterised as having a XPRD diffractogram as shown in FIG. 3. The Form III polymorph is further characterised as having a DSC endotherm onset of 235° C.

Compound (I) can also form solvates and hydrates, and these provide a further embodiment of the invention. These solvates and hydrates are unstable under certain conditions and generally revert to one of the polymorphic forms as defined above.

In a further embodiment the invention provides a hydrate of Compound (I), in particular the dihydrate of Compound (I).

In a further embodiment the invention provides a solvate of Compound (I), in particular a solvate selected from the dichloromethane, trichloromethane or 1,4-dioxane solvate of Compound (I).

The amorphous form of Compound (I) provides a further embodiment of the invention.

The Form II polymorph of Compound (I) exhibits surprisingly advantageous thermodynamic stability when compared to the Form 1 and Form III polymorphs in competitive slurrying experiments. The Form II polymorph of Compound (I) is therefore advantageous when formulated as dry powder compositions for inhalation, in particular for the treatment of respiratory indications.

In one embodiment the invention relates to a polymorph of (S)-3-(3-(1-methyl-2-oxo-5-(pyrazolo[1,5-a]pyridine-3-yl)-1H-imidazo[4,5-b]pyridine-3(2H)-yl)piperidin-1-yl)-3-oxopropanenitrile (Compound (I)) as a therapeutic agent, in particular the Form II polymorph. The polymorphs of the invention may be used to treat the diseases disclosed in WO2011/051452, in particular respiratory diseases. Particular diseases that may be treated with the polymorphs of the invention include asthma, COPD, pulmonary arterial hypertension (PAH), idiopathic pulmonary fibrosis (IPF) and lung cancer. In one embodiment the invention relates to the Form II polymorph of Compound (I) as a therapeutic agent. In one embodiment the invention relates to the use of Form II of Compound (I) for the treatment of respiratory diseases.

In one embodiment the invention relates to the Form II polymorph of Compound (I) for use in the treatment or prophylaxis of asthma or COPD, in particular severe asthma.

In a further embodiment the invention relates to a method of treatment of a respiratory disease which comprises administering to a patient in need thereof the Form II polymorph of Compound (I), optionally in the presence of a pharmaceutical carrier or excipient.

In a further embodiment the invention relates to the use of the Form II polymorph of Compound (I), in the manufacture of a medicament for treating respiratory diseases such as asthma or COPD, in particular severe asthma.

DETAILED DESCRIPTION

The polymorphs of the invention can be administered with one or more additional therapeutic agents, either simultaneously of sequentially. For respiratory indications the polymorphs of the invention can be administered in combination with a therapeutic agent selected from inhaled corticosteroid, ß-agonists, long-acting muscarinic agonists, PDE4 inhibitors, or a biological agent such as an agent active at the IL-13, IL-5, IL-4/13, IL-17, IL-25 or IL-33 receptors. In particular the polymorphs of the invention can be administered with one or more compounds selected from salbutamol, glycopyrrolate, pirfenidone, nintedanib, beclomethasone, fluticasone, budesonide, mometasone, tiotropium, formoterol, indacaterol, vilanterol, umeclidinium and roflumilast.

In one embodiment the invention provides the Form II polymorph of Compound (I) in combination with one or more additional therapeutic agents. In one embodiment the invention provides the Form II polymorph of Compound (I) in combination with one or more compounds selected from salbutamol, glycopyrrolate, pirfenidone, nintedanib, beclomethasone, fluticasone, budesonide, mometasone, tiotropium, formoterol, indacaterol, vilanterol, umeclidinium and roflumilast.

The polymorphs of the invention are administered as pharmaceutical compositions, typically with a pharmaceutically acceptable carrier or excipient. Suitable compositions can be in the form of tablets, capsules, liquid suspensions, topical compositions, transdermal compositions or inhalable compositions. Solid dosage forms in which the crystalline polymorph is maintained are desirable, and provide a further embodiment of the invention. In one embodiment the invention provides an inhalable composition comprising the Form (II) polymorph of Compound (I).

For the treatment of respiratory diseases inhalable compositions which can be delivered via a dry powder inhaler (DPI) form a further embodiment of the invention. Compositions in the form of a suspension for delivery via a pressurised metered dose inhaler (pMDI) form a further aspect of the invention.

In one embodiment the invention relates to a pharmaceutical composition comprising the Form II polymorph of Compound (I) with one or more pharmaceutically acceptable excipients.

For administration by inhalation using a dry powder inhaler, the polymorphs of the invention can be administered as dry powder formulations with one or more carrier substances. Suitable inhalation carriers are known in the art and in one embodiment include crystalline sugars such as monosaccharides or disaccharides. In one preferred embodiment the carrier is lactose.

Dry powder formulations of the invention may also have additional excipients such as force control agents. A force control agent is an additive which reduces the cohesion between the fine particles within the powder formulation. This promotes de-agglomeration when the powder is dispensed from the inhaler. Suitable force control agents are known in the art. In one embodiment the force control agent is a metal stearate such as magnesium stearate.

The dry powder formulations of the invention are typically formulated to have a particle size for inhalation. In one embodiment the polymorphs of the invention are formulated to have an average particle size of less than about 10 µm, in one embodiment less than about 5 µm and in a further preferred embodiment in the range of about 1 µm to about 5 µm.

In one embodiment the Form II polymorph is administered as a dry powder formulation with lactose, optionally magnesium stearate the formulation having an average particle size in the range of about 1 µm to about 5 µm.

The dry powder formulations of the invention can be administered using various dry powder inhalers such as GyroHaler® or a lever operated inhaler such as that disclosed in WO2009/092770. In a further embodiment the invention provides a kit comprising an inhaler in combination with a polymorph of Compound (I) and one or more pharmaceutically acceptable excipients. In a further embodiment the invention provides a kit comprising a dry powder inhaler in combination with the Form II polymorph of Compound (I) and one or more pharmaceutically acceptable excipients. In a further embodiment the invention provides a kit comprising a GyroHaler® dry powder inhaler in combination with the Form II polymorph of Compound (I) and one or more pharmaceutically acceptable excipients. In a still further embodiment the invention provides a kit comprising a lever operated dry powder inhaler disclosed in WO 2009/092770 in combination with the Form II polymorph of Compound (I) and one or more pharmaceutically acceptable excipients.

In a further embodiment the invention provides a process for the preparation of the Form II polymorph of (S)-3-(3-(1-methyl-2-oxo-5-(pyrazolo[1,5-a]pyridine-3-yl)-1H-imidazo[4,5-b]pyridine-3(2H)-yl)piperidin-1-yl)-3-oxopropanenitrile which comprises suspending the compound as an alternative form in a suitable solvent, optionally heating and then isolating the resulting product. In one embodiment the invention provides a process for the preparation of the Form II polymorph of (S)-3-(3-(1-methyl-2-oxo-5-(pyrazolo[1,5-a]pyridine-3-yl)-1H-imidazo[4,5-b]pyridine-3(2H)-yl)piperidin-1-yl)-3-oxopropanenitrile which comprises suspending the Form I in aqueous THF and heating the resulting slurry between ambient temperature and about 50° C. In one embodiment the aqueous THF contains water, for example about 5% water. The polymorph is typically isolated by filtration followed by drying.

The hydrates, solvates and amorphous form of (S)-3-(3-(1-methyl-2-oxo-5-(pyrazolo[1,5-a]pyridine-3-yl)-1H-imidazo[4,5-b]pyridine-3(2H)-yl)piperidin-1-yl)-3-oxopropanenitrile can be prepared using the techniques exemplified herein.

The following examples illustrate the invention.

EXAMPLES

The following examples illustrate the invention.

1. General Instruments and Methodology Details 1.1 X-Ray Powder Diffraction (XRPD)

X-Ray Powder Diffraction patterns were collected on a Bruker D8 diffractometer using CuKa radiation (40 kV, 40 mA), θ-2-θ goniometer, and divergence of V4 and receiving slits, a Ge monochromator and a Lynxeye detector. The instrument is performance checked using a certified Corundum standard (NIST 1976). The software used for data collection was Diffrac Plus XRD Commander v2.6.1 and the data were analysed and presented using Diffrac Plus EVA v13.0.0.2 or v15.0.0.0.

Samples were run under ambient conditions as flat plate specimens using powder as received. The sample was gently packed into a cavity cut into polished, zero-background (510) silicon wafer. The sample was rotated in its own plane during analysis. The details of the data collection are:
Angular range: 2 to 42°2θ
Step size: 0.05°2θ
Collection time: 0.5 s/step 1.2. Nuclear Magnetic Resonance (NMR)

NMR spectra were collected on a Bruker 400 MHz instrument equipped with an auto-sampler and controlled by a DRX400 console. Automated experiments were acquired using ICONNMR v4.0.7 running with Topspin v1.3 using the standard Bruker loaded experiments. For non-routine spectroscopy, data were acquired through the use of Topspin alone.

Samples were prepared in DMSO-d6, unless otherwise stated. Off-line analysis was carried out using Topspin v1.3 or ACD SpecManager v12.5 or ACD Labs 2012 release (build 61851).

1.3 Differential Scanning Calorimetry (DSC)

DSC data were collected on a Mettler DSC 823E equipped with a 34 position auto-sampler. The instrument was calibrated for energy and temperature using certified indium. Typically 0.5-3 mg of each sample, in a pin-holed aluminium pan, was heated at 10° C./min from 25° C. to 300° C. A nitrogen purge at 50 ml/min was maintained over the sample.

The instrument control and data analysis software was STARe v9.20.

2. Preparation of Polymorphic Forms of Compound (I)

2.1. Form I

The compound (S)-3-(3-(1-methyl-2-oxo-5-(pyrazolo[1,5-a]pyridine-3-yl)-1H-imidazo[4,5-b]pyridine-3(2H)-yl)piperidin-1-yl)-3-oxopropanenitrile Form I was prepared according to the procedures outlined in WO2011/051452.

Form I had DSC endotherm onsets of 142° C. and 235° C. and an exotherm onset of 155° C.

The product was identified as Form I and had an XRPD diffractogram as shown in FIG. 1 with peak data shown in the table below.

| Angle (°2θ) | Intensity | Rel. Intensity (%) |
|---|---|---|
| 3.90 | 410 | 24.1 |
| 4.35 | 280 | 16.5 |
| 4.85 | 328 | 19.3 |
| 9.99 | 295 | 17.3 |
| 11.14 | 561 | 33.0 |
| 14.04 | 1136 | 66.7 |
| 14.54 | 737 | 43.3 |
| 16.89 | 640 | 37.6 |
| 17.64 | 1702 | 100.0 |
| 19.54 | 286 | 16.8 |
| 20.04 | 380 | 22.3 |
| 20.69 | 169 | 9.9 |
| 22.14 | 1133 | 66.6 |
| 24.39 | 1396 | 82.0 |
| 24.93 | 923 | 54.2 |
| 25.88 | 281 | 16.5 |
| 26.23 | 832 | 48.9 |
| 29.98 | 171 | 10.0 |
| 31.63 | 215 | 12.6 |
| 34.88 | 186 | 10.9 |

2.2. Form II (S)-3-(3-(1-methyl-2-oxo-5-(pyrazolo[1,5-a]pyridine-3-yl)-1H-imidazo[4,5-b]pyridine-3(2H)-yl)piperidin-1-yl)-3- oxopropanenitrile Form I (500 mg) was suspended in THF+ 5% water (5.0 ml). The resulting slurry was shaken for 24 h, cycling between ambient temperature and 50° C. at 8 h intervals. The solid present was isolated by filtration and air dried to give 315 mg of an off white solid.

Form II had an endotherm onset of 239° C.

Form II had an XRPD diffractogram as shown in FIG. 2 with peak data shown in the table below.

| Angle (°2θ) | Intensity | Rel. Intensity (%) |
|---|---|---|
| 8.25 | 5933 | 100.0 |
| 10.80 | 1472 | 24.8 |
| 12.60 | 761 | 12.8 |
| 13.25 | 2310 | 38.9 |
| 15.40 | 3572 | 60.2 |
| 17.65 | 2549 | 43.0 |
| 18.35 | 420 | 7.1 |
| 18.80 | 1325 | 22.3 |
| 20.15 | 1081 | 18.2 |
| 20.70 | 1393 | 23.5 |
| 20.90 | 687 | 11.6 |
| 22.55 | 938 | 15.8 |
| 24.29 | 1301 | 21.9 |
| 24.74 | 480 | 8.1 |
| 25.39 | 2776 | 46.8 |
| 25.99 | 627 | 10.6 |
| 26.24 | 585 | 9.9 |
| 26.74 | 1481 | 25.0 |
| 27.34 | 451 | 7.6 |
| 32.99 | 542 | 9.1 |

2.3. Form III (S)-3-(3-(1-methyl-2-oxo-5-(pyrazolo[1,5-a]pyridine-3-yl)-1H-imidazo[4,5-b]pyridine-3(2H)-yl)piperidin-1-yl)-3-oxopropanenitrile Form I (250 mg) was placed in an oven at a temperature of 206° C. for 30 minutes. Material was then cooled to room temperature to give 250 mg of an off white solid.

Form III had an endotherm onset of 235° C.

Form III had an XRPD diffractogram as shown in FIG. 3 with peak data shown in the table below.

| Angle (°2θ) | Intensity | Rel. Intensity (%) |
|---|---|---|
| 6.75 | 458 | 9.8 |
| 8.70 | 710 | 15.1 |
| 11.40 | 2594 | 55.3 |
| 13.60 | 3965 | 84.5 |
| 14.85 | 498 | 10.6 |
| 15.25 | 324 | 6.9 |
| 15.60 | 1893 | 40.3 |
| 16.20 | 904 | 19.3 |
| 17.15 | 665 | 14.2 |
| 17.40 | 632 | 13.5 |
| 19.30 | 1056 | 22.5 |
| 20.45 | 1001 | 21.3 |
| 22.00 | 1463 | 31.2 |
| 22.80 | 4692 | 100.0 |
| 25.44 | 275 | 5.9 |
| 25.94 | 650 | 13.9 |
| 26.14 | 614 | 13.1 |
| 26.69 | 1871 | 39.9 |
| 29.64 | 273 | 5.8 |
| 31.74 | 263 | 5.6 |

3. Preparation of the Hydrate, Solvates and Amorphous Forms of Compound (I)

3.1 1,2 Dimethoxyethane Solvate

S)-3-(3-(1-methyl-2-oxo-5-(pyrazolo[1,5-a]pyridine-3-yl)-1H-imidazo[4,5-b]pyridine-3(2H)-yl)piperidin-1-yl)-3-oxopropanenitrile Form I (500 mg) was suspended in 1,2-dimethoxyethane (5.0 ml). The resulting slurry was shaken for 24 h, cycling between ambient temperature and 50° C. at 8 h intervals. The solid present was isolated by filtration and air dried to give 425 mg of an off white solid The solvate had endotherm onsets of 143° C. and 235° C. and an exotherm onset of 151° C.

3.2 Hydrate

Amorphous (S)-3-(3-(1-methyl-2-oxo-5-(pyrazolo[1,5-a]pyridine-3-yl)-1H-imidazo[4,5-b]pyridine-3(2H)-yl)piperidin-1-yl)-3-oxopropanenitrile was prepared by rapid concentration of a solution of the compound (1.2 g) in trichloromethane under vacuum at 50° C. A portion of the resulting glassy solid (270 mg) was suspended in water (2 ml), briefly sonicated and then shaken overnight at ambient temperature. The resulting solid was isolated by filtration and air dried to give 182 mg of an off-white solid.

The hydrate had endotherm onsets of 48° C. and 236° C. and an exotherm onset of 146° C.

3.2 CHCl$_3$ Solvate

A saturated solution was prepared by slurrying ca. 500 mg of (S)-3-(3-(1-methyl-2-oxo-5-(pyrazolo[1,5-a]pyridine-3-yl)-1H-imidazo[4,5-b]pyridine-3(2H)-yl)piperidin-1-yl)-3-oxopropanenitrile Form I in trichloromethane (2 ml) at ambient temperature for 30 minutes. After passing through a 1 µm glass filter, the filtrate was cooled to 5° C. for three days. After this time a solid had evolved. This was isolated by filtration and air dried to give 130 mg of an off-white solid.

The solvate had endotherm onsets of 141° C. and 238° C. and an exotherm onset of 168° C.

3.3 Dichloromethane Solvate

Amorphous (S)-3-(3-(1-methyl-2-oxo-5-(pyrazolo[1,5-a]pyridine-3-yl)-1H-imidazo[4,5-b]pyridine-3(2H)-yl)piperidin-1-yl)-3-oxopropanenitrile was prepared by rapid concentration of a solution of the compound (1.2 g) in DCM under vacuum at 50° C. A portion of the resulting glassy solid (400 mg) was suspended in DCM (5 ml), and stirred at ambient temperature for four hours. The resulting solid was isolated by filtration and air dried to give 242 mg of an off-white solid.

The solvate had endotherm onsets of 135° C. and 238° C. and an exotherm onset of 175° C.

3.4 1,4-Dioxane Solvate

A saturated solution was prepared by slurrying ca. 500 mg of (S)-3-(3-(1-methyl-2-oxo-5-(pyrazolo[1,5-a]pyridine-3-yl)-1H-imidazo[4,5-b]pyridine-3(2H)-yl)piperidin-1-yl)-3-oxopropanenitrile Form I in 1,4-dioxane (5 ml) at ambient temperature overnight. After passing through a 1 µm glass filter, the filtrate was allowed to evaporate overnight. The suspended solid present was isolated by filtration and air dried to give 52 mg of an off-white solid.

The solvate had endotherm onsets of 121° C. and 235° C. and an exotherm onset of 133° C.

4. NMR Data for the Polymorphs

Figure 4:
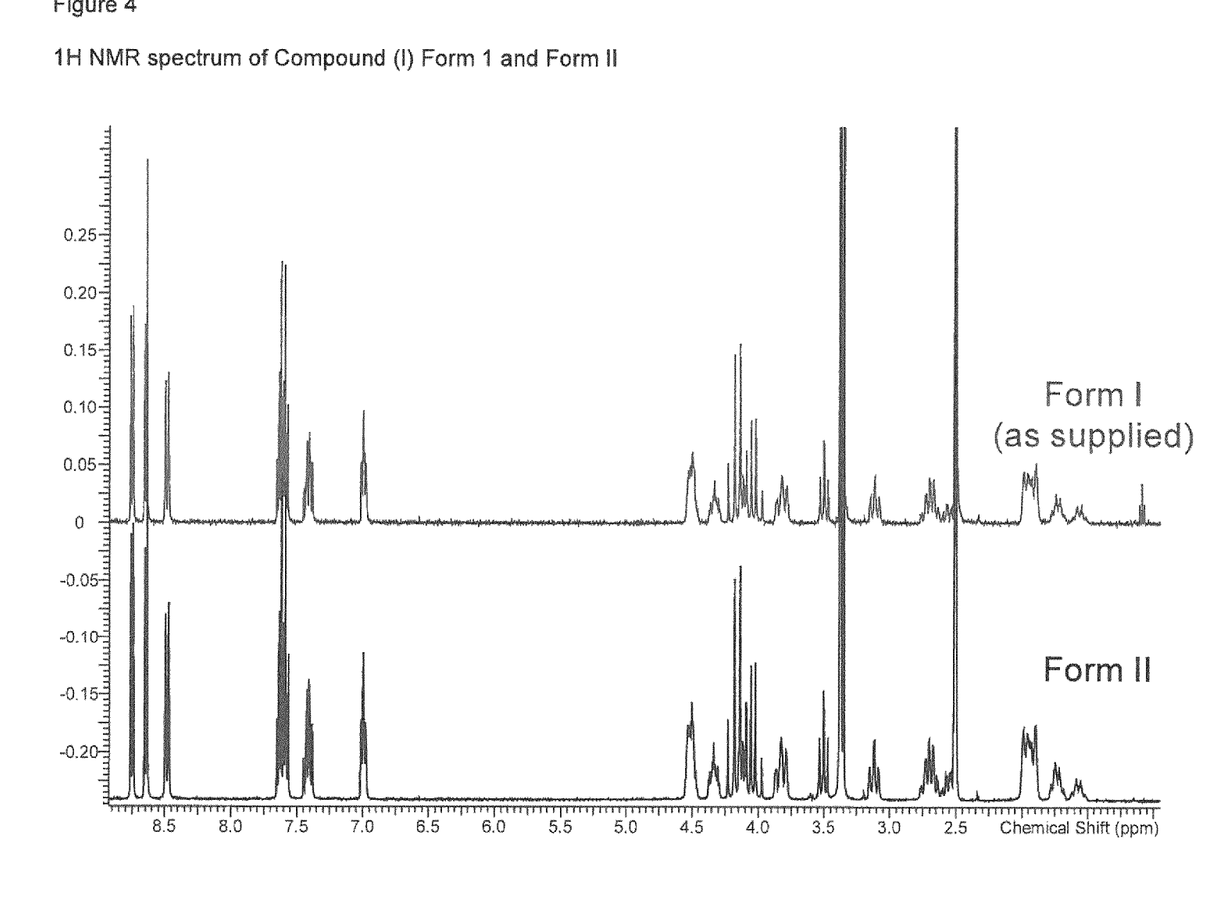
FIG. 4 shows the NMR spectrum of Compound (I) Form I and Form II.
Figure 5:
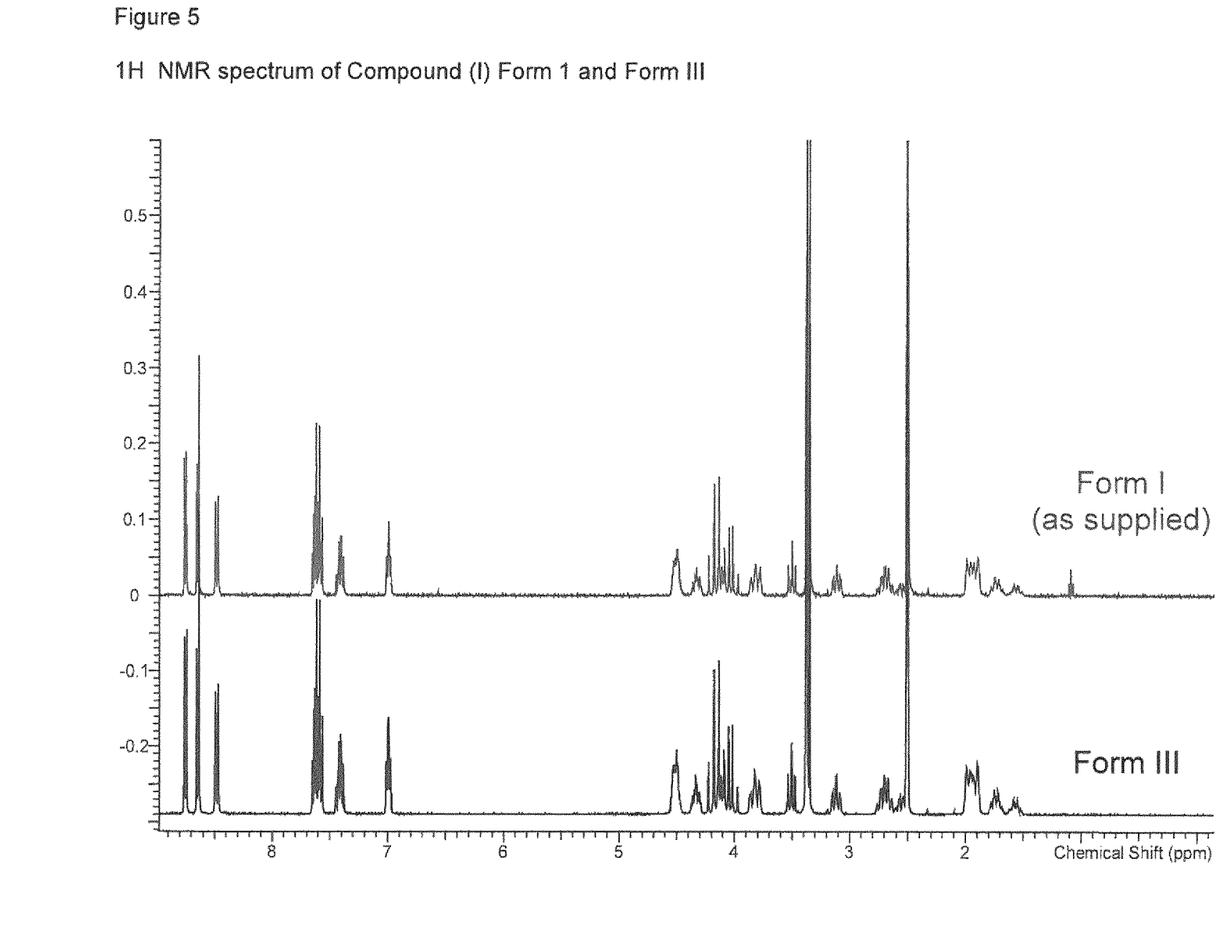
FIG. 5 shows the NMR spectrum of Compound (I) Form I and Form III.

1H NMR data demonstrated that the chemical structures of the Form I, II and III polymorphs were identical. See FIGS. 4 and 5.

5. Competitive Slurrying Experiments

Procedure 10 mg (+/−1 mg) each of the Form I, Form II, Form III, 1,2-dimethoxtethane solvate and the hydrate of (S)-3-(3-(1-methyl-2-oxo-5-(pyrazolo[1,5-a]pyridine-3-yl)-1H-imidazo[4,5-b]pyridine-3(2H)-yl)piperidin-1-yl)-3-oxopropanenitrile was added to each of twelve vials. To each vial was added 500 µl of the solvent system shown in the table below. The solvent systems used had been pre-saturated with (S)-3-(3-(1-methyl-2-oxo-5-(pyrazolo[1,5-a]pyridine-3-yl)-1H-imidazo[4,5-b]pyridine-3(2H)-yl)piperidin-1-yl)-3-oxopropanenitrile by shaking a slurry of Form I at the relevant temperature for 16 hours and then passing through a 1 µm glass filter.

The resulting slurries were agitated at the temperature shown for a period of one week. The solids present were then isolated by filtration, air dried and characterised by XRPD.

Results

| Vial Number | Solvent | Temperature (° C.) | XRPD characterisation |
| --- | --- | --- | --- |
| 1 | water | 5 | Form II/Hydrate* |
| 2 | water | 25 | Form II/Form III/Hydrate |
| 3 | water | 50 | Form II |
| 4 | MEK | 5 | Form II |
| 5 | MEK | 25 | Form II |
| 6 | MEK | 50 | Form II |
| 7 | EtOAc | 5 | Form II/1,2-dimethoxyethane solvate |
| 8 | EtOAc | 25 | Form II/1,2-dimethoxyethane solvate |
| 9 | EtOAc | 50 | Form II |
| 10 | IPA | 5 | Form II |
| 11 | IPA | 25 | Form II/1,2-dimethoxyethane solvate |
| 12 | IPA | 50 | Form II |

*poor recovery hampered interpretation

Of the three anhydrous forms, Form II is the most thermodynamically stable at all three temperatures evaluated. No Form I or Form III material was visible in any of the isolated solids, except one of the experiments in water. This is likely to be attributable to the poor solubility of the compound in water, slowing the rate of conversion.

The same result was observed for Hydrate I, with complete conversion to Form II observed in water at 50° C., but not at 25° C. or 5° C. No Hydrate was observed in any solvent system other than pure water, showing the hydrate to be less stable than the anhydrous Form II in organic solvents.

The results from the MEK experiments show that Form II can be reliably isolated even at sub-ambient temperatures.

The invention claimed is:

1. A polymorph of (S)-3-(3-(1-methyl-2-oxo-5-(pyrazolo[1,5-a]pyridine-3-yl)-1H-imidazo[4,5-b]pyridine-3(2H)-yl)piperidin-1-yl)-3-oxopropanenitrile with the following diffraction angles (2Theta) based on cupric Kα1:
   at approximately 8.25%;
   at approximately 13.25%;
   at approximately 15.40°;
   at approximately 17.65°; and
   at approximately 25.39°.

2. A polymorph according to claim 1 further characterised as having a XPRD diffractogram as shown in FIG. 2.

3. A polymorph according to claim 1 further characterised as having a DSC endotherm onset of 239° C.

4. A process for the preparation of the claim 1 polymorph of (S)-3-(3-(1-methyl-2-oxo-5-(pyrazolo[1,5-a]pyridine-3-yl)-1H-imidazo[4,5-b]pyridine-3(2H)-yl)piperidin-1-yl)-3-oxopropanenitrile which comprises suspending the compound as Form I in aqueous THF and heating the resulting slurry between ambient temperature and about 50° C.

5. The process according to claim 4 in which the aqueous THF comprises about 5% water.

6. A pharmaceutical composition comprising a polymorph according to claim 1 with one or more pharmaceutically acceptable excipients.

7. A composition according to claim 6 in which the excipient comprises lactose.

* * * * *

UNITED STATES PATENT AND TRADEMARK OFFICE
CERTIFICATE OF CORRECTION

PATENT NO. : 10,087,196 B2  
APPLICATION NO. : 15/547657  
DATED : October 2, 2018  
INVENTOR(S) : Alexander Munro

Page 1 of 1

It is certified that error appears in the above-identified patent and that said Letters Patent is hereby corrected as shown below:

On the Title Page

Item (72), Line 1, "Chippenham (GB)" should read -- Chippenham Wiltshire (GB) --.

Signed and Sealed this  
Ninth Day of April, 2019

Andrei Iancu  
*Director of the United States Patent and Trademark Office*